United States Patent [19]
Tayot et al.

[11] 4,303,638
[45] Dec. 1, 1981

[54] CHOLERA VACCINE

[75] Inventors: Jean-Louis Tayot, La Tour de Salvagny; Marie-Claude Mynard, Ste. Foy-les-Lepon, both of France

[73] Assignee: Institut Merieux, Lyons, France

[21] Appl. No.: 944,122

[22] Filed: Sep. 19, 1978

[30] Foreign Application Priority Data

Sep. 19, 1977 [FR] France ............................ 77 28162

[51] Int. Cl.³ ........................ A61K 9/32; A61K 9/58
[52] U.S. Cl. ...................................... 424/32; 424/35; 424/87; 424/92
[58] Field of Search ................ 424/20, 31, 32, 35, 424/125, 85–92

[56] References Cited

U.S. PATENT DOCUMENTS

| | | | |
|---|---|---|---|
| 2,952,585 | 9/1960 | Heller | 424/125 |
| 3,185,625 | 5/1965 | Brown | 424/35 |
| 4,125,492 | 11/1978 | Cuatrecasas et al. | 424/92 |
| 4,152,412 | 5/1979 | Brewer | 424/125 |

FOREIGN PATENT DOCUMENTS 1452648 10/1976 United Kingdom ................ 424/92

*Primary Examiner*—Delbert R. Phillips
*Assistant Examiner*—Blondel Hazel
*Attorney, Agent, or Firm*—Cushman, Darby & Cushman

[57] ABSTRACT

A particulate material for inducing immunity to cholera toxin comprises support particles provided with a first coating of a ganglioside having affinity for cholera toxin and a second coating of cholera toxin attached to said ganglioside coating. This particulate material can be used as an orally or parenterally administered medicine for humans to induce an immunity response to cholera toxin.

31 Claims, No Drawings

CHOLERA VACCINE

The object of this invention is a new particulate material, its preparation, and its application as a medicine.

It is known that in order to have an effective prevention of cholera it is necessary to acquire good immunity towards to the cholera toxin.

The object of the present invention is a new particulate material notably capable of inducing immunity and a synthesis of antibodies to the cholera toxin when administered to a living organism possessing an immunity defense system.

In particular, the object of the present invention is the provision of support particles covered by a first coating of ganglioside or one of its derivatives possessing affinity for the cholera toxin, and by a second coating of cholera toxin.

The particles used as supports may be red blood corpuscles of any animal species, bacterial germs, particularly cholera vibrios of the INABA or the OGAWA types, particles of organic polymers such as synthetic or natural latex, particles of granular or colloidal carbons, particles of polysaccharides or modified polysaccharides, porous mineral particles covered by polysaccharides or modified polysaccharides and in general, any other type of particles to which at least one of the methods of ganglioside or ganglioside derivative affixing applies.

The porous mineral particles mentioned previously are among others: metallic oxides such as silica, alumina, magnesia, titanium oxide or their synthetic or natural derivatives such as glass, silicates, borosilicates or kaolin.

In this application, "cholera toxin" refers to not only the toxic form as such, or choleragen, but also to the non toxic form known as choleragenoid. It is known that choleragen transforms to choleragenoid naturally and progressively when exposed to heat. Both choleragen and choleragonoid are present in the culture filtrates of cholera vibrios.

It is known that among the various gangliosides, the ganglioside $G_{M1}$ and certain of its derivatives have a strong and specific biochemical type of affinity for the choleragen and the cholderagenoid. This affinity is also observed with certain ganglioside $G_{M1}$ derivatives.

It is especially the case of the lysoganglioside $G_{M1}$. The lysoganglioside is obtained by alkaline hydrolysis of the ganglioside $G_{M1}$ according to the method described by HOLMGREN, MANSSON AND SVEN-NERHOLM, Medical *Biology* (1974), 52, 229–233. The goal of this alkaline hydrolysis is to transform the two N-acetyl functions and the N-acyl function of the ganglioside $G_{M1}$ into amino, $NH_2$, functions.

Other ganglioside derivatives also have an affinity for the cholera toxin.

In this application, the term "ganglioside $G_{M1}$ derivative" will refer to any ganglioside derivative which has an affinity for the cholera toxin, and in particular the products resulting from a partial or total hydrolysis of the N-acyl or N-acetyl groups of the ganglioside $G_{M1}$ into -$NH_2$ groups, but also the mono- or a -sialo gangliosides resulting from the acid treatment of the gangliosides or their derivatives, in particular those resulting from the total or partial hydrolysis of the N-acyl or N-acetyl groups.

The size of the particles in accordance with the present invention may vary from 0.1 to 1000$\mu$.

The invention also has as an objective the preparation process for the particulate material referred to above. This process consists, in its first stage, in affixing ganglioside $G_{M1}$ and/or its derivatives on the support particles. This fixation may be achieved either by establishing a chemical bond or by taking advantage of any affinity phenomena, such as one of adherence.

The second stage of the patent process consists of affixing the cholera toxin on the particles covered with ganglioside $G_{M1}$, or one of its derivatives.

Generally, when particles covered by ganglioside $G_{M1}$ or lysoganglioside $G_{M1}$ have been prepared according to the above description, it is very easy and quick to prepare the special cholera toxin covered material. In fact, simple incubation with the culture filtrate, followed by centrifugation are enough to obtain a purification and a concentration of the toxin on the particles. The residue on the surface may thus be completely eliminated in one stage of the toxin, whereas generally all the other useless macro-molecules are left. In fact, the toxin concentrates by itself on the particles due to the very strong affinity of particulate ganglioside or lysoganglioside $G_{M1}$ for the choleragen and the choleragenoid.

For the fixation of the cholera toxin coat (second stage of the process) the particles coated with ganglioside $G_{M1}$ and/or one of its derivatives are left in contact during a sufficient time to obtain, as desired, either saturation or partial covering of the reactive sites (ganglioside $G_{M1}$ or its derivatives) by the toxin. This time generally varies from 1 to 60 minutes, at temperatures ranging from 0° to 60° C.

The particulate material which is the object of this invention is notably formed by red blood corpuscles onto which are attached a first coating consisting of the ganglioside $G_{M1}$ or one of its derivatives and a second coating which consists of choleragen, choleragenoid or their mixtures.

The red blood corpuscles are first treated with a carbonyl derivative before receiving the two coatings.

The carbonyl derivative is preferably formaldehyde or glutaraldehyde.

The invention also has as its objective the preparation process for this particulate material consisting of coated red blood corpuscles.

This process consists, first, in reaching of suspension of a red blood corpuscle in physiologic water with a carbonyl derivative, for example a solution in the physiologic water of said carbonyl derivative, and then contacting the product thus obtained with a solution containing choleragen, choleragenoid, or their mixtures.

"Physiologic water" refers to an aqueous solution with a sensibly balanced pH containing around 9 g/l of sodium chloride.

Preferably, the red blood corpuscles are left in contact with the carbonyl derivative for 15 minutes to 15 hours with a temperature varying from 0° to 60° C. After this the red blood corpuscles are then washed with distilled water and dissolved in the physiologic water.

Generally, the amount of carbonyl derivative may vary from 0.01 to 20 grams for each 100 ml. of red blood corpuscle suspension.

When affixing the ganglioside $G_{M1}$ to a previously treated red blood corpuscle suspension a ganglioside solution with a pH equal to or superior to 8 is added.

Preferably, to attach the ganglioside $G_{M1}$ the pH should be about 13. The incubation temperature may vary between 0° and 60° C., preferably around 45° C. The incubation time is generally at least one hour and preferably around 15 hours.

The suspension is then centrifuged and the centrifugation residue is washed and suspended in physiologic water.

In order to affix the lysoganglioside $G_{M1}$ on the red blood corpuscles, the following procedure is employed: a solution of lysoganglioside $G_{M1}$ with a pH above 5 and preferably around 7 is added to the red blood corpuscle suspension which has been treated with the carbonyl derivative. Preferably, the incubation temperature varies between 0° to 60° C. for an interval ranging from 30 minutes to 3 hours.

The suspension then undergoes centrifugation and the residue is collected, washed and suspended in physiologic water.

It has been observed that it is possible to attach lysoganglioside $G_{M1}$ directly onto the fresh red blood corpuscles. However, it is possible to observe frequent hemolysis phenomena especially for strong doses of lysogangliosides. Therefore, it is preferable to improve the reaction, as previously described, by pretreating the red blood cells with the carbonyl derivative so as to make them insensitive to any hemolitic influence.

It has been verified that the aldehyde functions present on the red blood cells which have been treated with the glutaraldehyde do not intervene in the fixation reaction of the ganglioside. As a matter of fact, it was surprisingly discovered that if prior chemical neutralizing of the aldehyde functions, by adding a glycocoll solution (20 g. per liter) with a pH between 7 and 11 is achieved, this treatment will have no bearing on the ulterior fixation of the ganglioside at an alkaline pH.

The particulate material of this invention may be prepared with any type of red blood corpuscles, i.e. human, sheep, monkeys, rabbits, dogs, goats, cows, horses, hens, pigeons, geese, etc.

After so obtaining red blood corpuscles covered with a first layer of ganglioside $G_{M1}$ or lysoganglioside, the red blood corpuscles are then contacted with a solution containing cholera toxin. Because of the specific affinity of the ganglioside $G_{M1}$ for the cholera toxin the solution may be an impure solution, for example a filtrate of crude culture of cholera vibrios. The fixation on the first coating (gangliosides) by a second coating (cholera toxin) is thus obtained.

For the fixation of a second coating, which is the second stage of the process, the red blood corpuscles covered with the first coating are left in contact with the toxin solution during a period varying from 1 to 60 minutes at a temperature ranging from 0° to 60° C. and preferably between 20° and 45° C.

The particles must then be separated by the usual processes, for example centrifugation, washing in order to eliminate the impurities present and suspension in physiologic water, or lyophilization.

The particulate material of this invention may also be produced with bacteria as support particles.

The technique for the fixation of lysoganglioside $G_{M1}$, or its derivatives on the bacterial germs is analogous to the one already described for the red blood corpuscle fixation.

Before affixing the ganglioside $G_{M1}$ or its derivatives, the vibrios must be inactivated by treating them with a carbonyl derivative such as formaldehyde or glutaraldehyde under the same conditions as those described for the red blood corpuscles.

In the experimental section which follows, the fixation technique for ganglioside $G_{M1}$ and lysoganglioside $G_{M1}$ on such particles is described, by using cholera vibrio as an example.

The particulate material of this invention may also be obtained by using as support organic polymer particles such as natural or synthetic latex.

Generally, it is possible to use those organic polymer particles likely to remain in stable homogenous suspension in water, because of the presence of a detergent, preferably an anionic detergent. For example it is possible to use vinyl monomers, such as styrene, butadiene, divinylbenzine, etc. possibly having other chemical functions such as alcohol, amino, epoxide, carboxylic acid, sulphonic acid and corresponding esters.

It has been observed that the ganglioside $G_{M1}$ fixation on the latex particles followed the same rules as the fixation on red blood corpuscles. In particular, it was noted that it was necessary to operate at an alkaline pH to couple the ganglioside $G_{M1}$, but that this alkaline pH is not necessary to couple the lysoganglioside $G_{M1}$. The toxin fixation is achieved in an manner analogous to that previously described.

For latex, the pretreatment with a carbonyl derivative generally becomes useless. However, for latex having $NH_2$ functions this pretreatment allows a chemical activation of the support.

Generaly the fixation of ganglioside or its derivatives on the particles is probably due to an incorporation of the hydrophobic sites of the ganglioside in the hydrophobic sites of the support particles. This process, which is enough by itself, may be completed by a chemical coupling reaction with the reactive functions eventually present on the surface the particles.

The particulate material of this invention may also be produced with active carbon particles.

For colloidal carbon particles, analogous to those found in India ink, the same techniques as those described for latex may be applied. For larger active carbon particles, ranging from 1 to 10$\mu$, the fixation technique is even simpler due to the considerable adsorbing power of these particles. Even the ganglioside $G_{M1}$ is adsorbed just as well at neutral pH as at an alkaline pH. The fixation of the toxin is achieved in an manner analogous to that described above.

The particulate material of the invention may be produced with the help of polysaccharide particles which include visible particles or even soluble macromolecules which are therefore invisible. The term "polysaccharide" here includes the modified polysaccharides. These polysaccharides are, in particular, dextran, celluloses, starch, agarose, etc. or even modified polysaccharides such as dialkylaminoalkyl—or di(hydroxyalkyl) amino alkyl polysaccharides i.e., diethylaminoethyl dextran, diethylaminoethyl cellulose, etc.

The polysaccharides may also be used, not as particles, but as a coating on the mineral particles, in particular mineral oxides such as those mentioned above.

The porous mineral particles covered by polysaccharides or modified polysaccharides may be those described in the French Pat. No. 76.23176 or those described in the French patent application introduced by Marie Claude Mynard the same day as the present application and entitled: "New matter capable of affixing in a reversible manner biologic macromolecules; its preparation and its application."

The mineral particles covered by polysaccharides according to the French patent application No.

76.23176 are formed by a porous mineral support, such as a porous mineral oxide, coated directly on the surface with an amino polysaccharide polymer.

The porous mineral support may be silica, alumina, magnesium, a titanium oxide or their derivatives, natural or synthetic such as glass, borosilicates, silicates, kaolin, etc.

The amino polysaccharide polymer is attached to the porous mineral support by adhesion.

The internal surface of the porous mineral support is preferably lower or equal to 100 m²/g and if possible between 5 and 80 m²/g. The average porous diameter is preferably higher or equal to 25 nm and if possible between 50 and 1000 nm. For larger surfaces or smaller pore diameters the internal support surface becomes inaccessible to the polysaccharide polymer. Preferaly in this invention the porous mineral support is silica or alumina and particularly a porous silica support having an anionic character obtained thru the process described in the French Pat. Nos. 1,473,239; 1,473,240; 1,475,929; 1,482,867. For example, porous silica marketed by "RHONE-POULENC CHIMIE/FINE" under the denominations: SPHEROSILS XOB 030, XOB 015, and XOB 005, having 50, 25 and 10 m²/g as respective surfaces can be used.

The polysaccharide polymer which is used to impregnate and coat the internal surface of the porous mineral support must have a strong cationic character and have good hydrophilic properties. It must have a molecular weight equal to at least $10^4$ daltons and if possible be between $10^5$ and $10^6$ daltons. It may have any formula, it may especially be an amino dextran derivative, starch derivative, cellulose derivative, agarose derivative or a natural or synthetic polymer, and any known monosaccharoses.

The amino functions of the polysaccharide polymer may be primary, secondary, tertiary or eventually quaternary.

The amino polysaccharidic polymer may corresponds to the following formula

in which:
R represents a polysaccharide residue, such as dextran, starch, cellulose or agarose residue,
n is a number from 1 to 10, preferably from 2 to 5 and
$R_1$ and $R_2$ which can be identical or different represent lower alkyl or lower hydroxyalkyl, for example the following radicals:

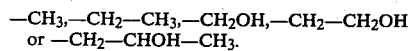

These polymers may be quaternized with the help of a known quaternizing agent such as alkyl halide or hydroxyalkyl halide, dimethyl sulfate, etc.

Among these polymers, it is worth mentioning the compounds known as DEAE DEXTRAN (diethylamino ethyl dextran) having a molecular weight of 500,000 and QAE DEXTRAN (quaternized dyethylamino ethyl dextran) sold by "PHARMACIA" and the compound known as DEAE starch (diethylamino ethyl starch) as well as the cationic starches such as those sold under the tradename "CATO" by the "ROQUETTE NATIONAL" Company.

The amino polysaccharide polymer may be reticulated with the help of a reticulating agent such as 1,4-butanediol diglycidyl ether, epichlorhydrin, epibromhydrin, or a diepoxide of formula II:

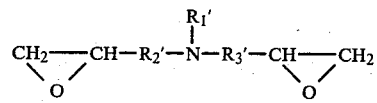

in which:
$R'_1$ is alkyl having 1 to 20 carbon atoms, preferably a lower alkyl having 1 to 4 carbon atoms.
$R'_2$ and $R'_3$ represent a hydrocarbon chain of 1 to 10 carbon atoms and preferably lower alkylene, for example the diepoxide of the formula:

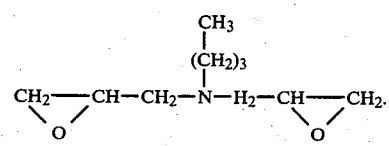

The preparation process for these amino polysaccharide coated particles may be implemented using two different methods: column impregnation and oven impregnation. These two methods are briefly described below.

According to the first method, the dry and homogeneous porous mineral oxide powder is directly poured into a chromatography column. The amino polysaccharide polymer is then introduced in a solution excess polymer is then eliminated thru elution with the help of a buffer.

According to the second method, i.e., oven impregnation, the porous mineral oxide is weighed and impregnated, cold or hot with an amino polysaccharide polymer aqueous solution. It is then dried in an oven at a temperature of 50° to 120° C. until it reaches a constant weight.

It is possible, after the impregnation with one of the methods just described and having obtained an homogenous powder after drying in the oven at 50° to 80° C., to treat this product with a solution of a reticulating agent in a volatile solvent such as ethyl ether for example.

Any of those previously mentioned may be used as reticulating agent.

After the evaporation of the solvent it is brought to a temperature between 40° and 120° C. preferably during 15 hours.

The porous mineral particles covered by modified or non-modified polysaccharides, as in the French patent application-introduced the same day as this one and to which previous reference has been made, consist of a porous mineral support covered by a polysaccharide polymer, for example an amino polysaccharide of formula I, the said polysaccharide coating being stabilized by reticulation, if necessary. And onto this polysaccharide or modified polysaccharide coating is grafted lysoganglioside $G_{M1}$ or any other partially or totally hydrolyzed derivative of ganglioside $G_{M1}$ as described above, having the schematic formula: $R''$—$NH_2$. $R''$ is the residue of the molecule of ganglioside $G_{M1}$ derivative or of lysoganglioside $G_{M1}$, the grafting liaison of said molecular corresponding to the schematic formula IV:

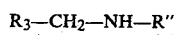

R" being defined above and R$_3$—CH$_2$— representing the residue of the polysaccharide polymer or the modified polysaccharide when it has been subject to an oxidative scission reaction followed by reduction.

The porous mineral support is notably constituted by a metallic oxide such as silica, alumina, magnesium or a titanium oxide, or by their natural or synthetic derivatives such as glass, silicates, borosilicates, kaolin, etc. The polysaccharide polymer is notably cellulose; the modified polysaccharide polymer is notably diethylaminoethyldextran, diethylaminoethyl starch or the diethylaminoethylcellulose; the modified or non-modified polysaccharide polymer is, if necessary, stabilized by reticulation, the reticulation agent being a dicarbonyl compound, a halohydrin or a diepoxide, notably 1,4-butanediol diglycidyl ether, epichlorohydrin, epibromohydrin, or a formula II epoxide, as defined previously.

The preparation process, as described in the French patent application, introduced on the same day as this one, is characterized by the coating of the porous mineral support by a polysaccharide polymer or a modified polysaccharide polymer; the polysaccharidic coating may be transformed into a modified polysaccharide coating if desired, a reticulation treatment is carried out to stabilize the coating if necessary, The said polysaccharide or modified polysaccharide coating may be subjected to an oxidative scission reaction according to established methods, the oxidation product is reacted with the lysoganglioside G$_{M1}$ or any other ganglioside G$_{M1}$ derivative as defined above, having the schematic formula R"-NH$_2$, the imine derivative obtained is then subject to a reducing agent capable of reducing the imine bond into an amine bond.

The process described above consists particularly in affixing the lysoganglioside G$_{M1}$ or any other G$_{M1}$ derivative, as define previously, onto the polysaccharide or modified polysaccharide by the following reactions:

(a) oxidative scission of the alpha-glycol groups to produce carbonyl derivatives which may be schematically represented by the formula R'$_4$—CHO, R'$_4$ being the residue of the polysaccharide molecule after The oxidative scission reaction;

(b) reaction of the ganglioside G$_{M1}$ derivative of the formula R"NH$_2$ with the carbonyl groups, according to the as the reaction:

R'$_4$—CHO+R"—NH$_2$→R'$_4$—CH=N—R"+H$_2$O and thereafter (c) reduction of the imine bond to a stable amine bond, for example by nascent hydrogen, in accordance with the reaction:

R'$_4$—CH=N—R'+2H→R$_3$—CH$_2$—NH—R",

R$_3$ being previously defined.

These various chemical transformations may be carried out at room temperature in a chromatographic column.

For the oxidative scission reaction, periodic acid or one of its derivatives may be used, as an alkaline periodate or lead tetraacetate.

For the reduction reaction a hydride, such as sodium borohydride, may be used.

To carry out the coating of the porous mineral support with the polysaccharide polymer or with a modified polysaccharide polymer, one may proceed as described in the French patent application No. 76.23176, that is the porous mineral support is introduced into a chromatographic column as a powder, a pH3 to 12 buffer is used until equilibrium is reached, said polymer solution is introduced in the same buffer, then it is eluted until the absence of polymers in the eluate, or else the porous material support is impregnated with an aqueous solution of said polymer, at a pH between 3 to 12, and then dried in an oven at a temperature of 50° to 120° C. until the weight is constant.

To obtain a cellulose coating, it is better to operate as follows: the porous mineral support is impregnated with a cellulose ester solution, it is dried and the coated support is then subject to an alkaline aqueous solution to hydrolize the ester groups. A porous mineral support coated with the cellulose regenerated as above is so obtained. The cellulose coating obtained in this manner is very stable and it coats perfectly the pores of the porous mineral support. It is useless to stabilize this coating by reticulation.

The polysaccharide polymer or modified polysaccharide which is used to impregnate and coat the internal porous mineral support surface has a molecular weigh of at least 10$^4$ daltons and preferably between 10$^5$ to 10$^6$ daltons.

To affix the cholera toxin on the particles constituted or coated with lysoganglioside G$_{M1}$ or its derivatives, the same process as the one described above for coated red blood corpuscles is used.

The present invention also has as an objective the application of the special cholera toxin covered matter. This application consists in its administration to human beings, possessing a defense system, in order to induce the formation of antibodies.

After being injected in animals it has been noted that the particulate material of this invention is capable of inducing an active synthesis of cholera antitoxin antibodies at very high rates. These antibodies may be isolated from the blood by known methods. The attainment of such antibodies is interesting because they are used notably as reagents in serology.

For animals susceptible to cholera, as well as for humans, this application constitutes a vaccine.

Therefore, this invention also has as an objective the medicinal application of the particulate material described above.

This medicine, as a vaccine, may be administered orally; when the material of this invention is produed on bacterial germs and particularly on inactivated vibrios, or based on soluble polysaccharides or soluble modified polysaccharides, it may also be administered parenterally, particularly subcutaneously.

The process of vaccination of the invention consists in administering, once or several times, a dose of the particulate material capable of inducing an immunity response by the formation of antibodies.

Moreover, when administered orally to humans carrying vibrios and possibly having or almost having cholera or related diarrhea, the particulate material of the this invention allows a stimulation of the immunity, particularly of the digestive and intestinal mucous membrane.

In addition, when the persons have already been vaccinated previously, either parenterally or orally, against cholera with the help of a purified and inactivated toxin preparation and/or with the vaccine described in this invention, the particulate material of this invention, administered orally makes it possible to achieve, as far as the digestive mucous membranes are concerned, an immunity booster effect.

It must be noted that when using carbon or latex based particles in particular, it is possible to affix, in addition to the cholera toxin, other macromolecules present in the culture filtrates of cholera vibrios. Because of this the immunity induced by these particles, although less specific than for other particles, may confer certain advantages, in the event where immunity against toxin alone was not sufficient.

It must also be noted that it is possible to produce ganglioside $G_{M1}$ or lysoganglioside covered particles without cholera toxin saturation. The oral administration of non cholera toxin saturated particles to a cholera threatened individual allows for a double protection, as it allows the induction of the sought after immunity on the one hand and it also protects temporarily the individual against any cholera toxin secretion by the vibrios possibly found in the intestine, because this cholera toxin preferably adheres to the ganglioside or lysoganglioside $G_{M1}$ coated sites which have not been saturated by the cholera toxin.

In fact by the presence of ganglioside $G_{M1}$, or of one of its derivatives, linking the cholera toxin to the particle, the toxin is at the same time automatically inactivated. In fact it is possible to observe that the particulate material so obtained lacks the toxic properties inherent in cholera toxin.

Because cholera toxin is combined with a particle, the toxin is more easily identified by the immunity cells of the organism. The particle therefore acts not only as a vaccinating principle but also as a stimulating principle.

The present invention also has as an objective the particulate material described above for use as a medicine and particularly as a vaccine.

The medicine may be provided either in powder form (lyophilized for example) or as a suspension or a solution to be administered directly.

The following non-limiting examples illustrate the invention.

EXAMPLE 1

Fixation of cholera toxin on porous silica coated with 1,4-butanediol diglycidyl ether reticulated DEAE dextran and then coated with ganglioside.

Starting with 2.2 lbs. of calves brains, about 7 liters of an aqueous extract is prepared in accordance with the process described by L. Svennerholm: Gangliosides, isolation methods in carbohydrate chemistry, vol. 6, edition R. L. Whistler and J. N. Bemiller, Acad. Press, New York 1972).

This aqueous extract is directly passed over a column of 50 g. of a support described in example 3 of French patent application No. 76.23176, previously equilibrated with 0.05 M TRIS-HCl buffer of pH6.8. The yield is 200 ml/cm²/hr. The gangliosides, about 40% of which are $G_{M1}$, affix themselves on the support under these conditions. A previous wash with the following solutions and in the following order:

TRIS-HCl 0.05 M, pH 6.8
NaOH 0.1 N
H₂O
Chloroform-Methanol-water in the following respective proportions (30-60-25), allows the elimination of numerous impurities. Having thus affixed the ganglioside on the particulate support, the cholera toxin is affixed as follows:

The particulate product obtained in the preceeding stage is incubated with cholera toxin at room temperature for a few minutes. After centrifugation, the residue is then washed with a 9 g/liter solution of sodium chloride to eliminate the non affixed proteins on the lysoganglioside $G_{M1}$. Finally, a 10% particle suspension is obtained. This suspension may be lyophilised.

EXAMPLE 2

Grafting of lysoganglioside $G_{M1}$ onto a porous mineral support impregnated with subsequently crosslinked; diethylaminoethyl dextran followed by fixing of cholera toxin.

2.1—the DEAE dextran based support is prepared according to one of the techniques mentioned in French patent application No. 76.23176.

10 g. of Spherosil XOB 030 is added to 30 ml. of a 7.5% strength DEAE dextran solution having a pH of 11.5. It is then all dried at 80° C. overnight then a butanediol diglycidyl ether at 1.5% in ethyl ether is added. The ether is evaporated under a draft, then it is all placed at 80° C. for 15 hours, to obtain the DEAE dextran reticulation.

2.2 The ganglioside solution is prepared by ion exchange chromatography on the porous DEAE dextran impregnated silica according to the method described in the previous example.

The crude ganglioside solution thus obtained contains about 40% of useful ganglioside $G_{M1}$ in the present application.

The two N-acetyl functions and the N-acyl groups of the ganglioside $G_{M1}$ are then hydrolyzed to amino NH₂ functions, by alkaline hydrolysis as previously described (HOLMGREN-MANSSON-SVENNERHOLM, Medical Biology (1974), 52 229–233). The product thus obtained is called lysoganglioside, it has three NH₂ functions per molecule. After lyophilization the powder obtained is dissolved in a 0.01 M carbonate buffer of a pH 9 having 20 g/l of NaCl, the concentration of powder being 1 mg/ml. 1 ml of this solution contains about 370 μg of sialic acid per ml.

2.3 Periodic oxidation of the support.

To the 10 g of Spherosil XOB 030 impregnated with subsequently crosslinked DEAE dextran, are added 0.02 M aqueous solution of sodium (pH around 4.5) periodate having a pH around 4.5. The oxidation period is 2 hours; room temperature is very appropriate for this operation.

The support is then washed in a 0.01 M (pH 9) sodium carbonate solution, to which 20 g/l sodium chloride have been added. The high ionic strength of this buffer is intended to saturate the cationic group of the oxidized and reticulated DEAE dextran with Cl ions and to prevent them from fixing the lysoganglioside by electro-static forces which could disturb the reaction of the amino groups at the aldehyde functions of the support.

At this stage, it is easy to demonstrate the presence of the aldehyde functions of the oxidized support. In the presence of Schiff reagent, a purplish pink color develops.

2.4 Lysoganglioside grafting. The preceeding support is washed, then 50 ml. of the lysoganglioside $G_{M1}$ solution are added. After a contact period of 2 hours, the contact surnatant is decanted. It is easy to show that almost all of the lysoganglioside (95 to 100%) has been coupled by using a dosage of sialic acid.

The support is rinsed with a carbonate buffer of pH 9. At this stage it is also easy to show that the support color with the Schill reagent is much weaker than in the preceding step, indicating a good lysoganglioside fixation to the aldehyde functions of the oxidized support.

2.5 Reduction by sodium borohydride. 50 ml of a 0.2 M solution of $NaBH_4$ in water are added to the preceeding support. After a 2 hour contact period at room temperature, the support is rinsed with water and then made into a column.

After equilibration in the chosen chromatography buffer (0.01 phosphate buffer with a pH of 7.2, containing 20 g/l of NaCl), the biospecific affinity column is ready to be used.

At this stage it is no longer possible to detect any trace of the aldehyde function by using the Schill reagent. The aldehyde functions which have not reacted with the lysoganglioside are themselves transformed into primary alcohol functions.

2.6 Fixation of the cholera toxin. To affix the toxin one proceeds in a similar manner to that described in example 1.

EXAMPLE 3

Grafting of lysoganglioside $G_{M1}$ to a cellulose impregnated porous mineral support, followed by fixation of the cholera toxin.

3.1 Cellulose impregnation 10 g of Spheresil (or any other porous mineral support) are added to 30 ml of a 3% solution of cellulose acetate in acetone. Cellulose propionate or other esters which are soluble in a solvent and are hydrolyzable may be used as well as long as they may revert to the original cellulose by alkaline hydrolysis.

The whole is dried with a warm draft. The powder may then be sifted, if needed, and made into a column.

The material is then washed continuously overnight with 10 liters of an aqueous 0.1 N NaOH solution at a rate of 500 ml/hr. After this alkaline hydrolysis, the column may be washed with acetone or any pH water, the cellulose so regenerated is no longer soluble and remains inside the pores of the porous mineral support, which it coats in as much as the initial polymer has reached all of the internal surface. The use of low molecular weight cellulose esters is advised for this reason.

3.2 Preparation of the solution of lysoganglioside $G_{M1}$ possessing amino functions.

The same conditions as in paragraph 2.2 of the preceeding example are used.

3.3 Periodic oxidation of the support uses the same conditions as in paragraph 3.

3.4 Lysoganglioside grafting. The same conditions as in paragraph 2.4 are used.

3.5 $NaBH_4$, sodium borohydride reduction. The same conditions as in paragraph 2.5 are used.

3.6 Fixation of the cholera toxin. The same conditions as in example 1 are used.

EXAMPLE 4

Fixation of the lysoganglioside $G_{M1}$ to red blood corpuscles previously treated with a carbonyl derivative followed by the cholera toxin fixation.

4.1 Sheep red blood corpuscles are washed 4 times in physiologic water (pH 7.2, 9 g of NaCl) to obtain a perfectly clear supernatant liquor from the final wash.

The red blood corpuscles are brought to a concentration of 8% in physiologic water and an equal volume of a 3% formaldehyde solution in physiologic water is then added.

After an 18 hour incubation at 37° C., the formol treated red blood corpuscles are washed four times in distilled water, then brought to 10% in physiologic water.

4.2 Glutaraldehyde treatment of the red blood corpuscles.

Sheep red blood corpuscles are washed 4 times in physiologic water and then brought to a 10% concentration and finally 1/20th of the volume of a 5% glutaraldehyde solution in physiologic water at pH 7.2 is added.

After an incubation period of 2 hours at room temperature, the glutaraldehyde treated red blood corpuscles are washed in distilled water, then brought to 10% in physiologic water.

4.3 Fixation of the ganglioside $G_{M1}$ on carbonyl derivative treated red blood corpuscles.

The red corpuscles treated with formol or glutaraldehydes previously obtained are washed in a 0.1 N NaOH solution, or in any basic solution with an alkaline pH greater or equal to 8 and preferably equal to at 13.

One volume of this 10% suspension is incubated with one volume of a ganglioside solution in a 0.1 N sodium hydroxide solution 0.1 N containing 100 mg of sialic acid per ml, that is to say around 0.5 mg of ganglioside $G_{M1}$/ml.

The incubation temperature may vary from 0° to 60° C. but is preferably 45° C.

The contact period is maintained for more than an hour, preferably for 15 hours.

The suspension is then centrifuged, the sialic acid dosage in the supernatant liquor allows a 50% estimated rate of fixation of ganglioside on the red corpuscles.

After 3 washes in physiologic water, the final solution is taken and kept at a 10% concentration.

4.4 Lysoganglioside $G_{M1}$ fixation on the carbonyl derivative treated red blood corpuscles.

To a 10% suspension of formol or glutaraldehyde treated red corpuscles prepared as before are added 2 mg. of lyophilized powder of ganglioside $G_{M1}$. A 0.1 mg to 10 mg. amount usually also gives satisfactory results. The incubation pH is 7.2, but it may also be alkaline as in the preceeding method.

The incubation period varies from 30 minutes to 3 hours.

The incubation temperature may vary from 0° to 60° but was chosen at 37° C.

After centrifugation, the coupling supernatant liquor only has 1 to 5% of the initial lysoganglioside, which shows the effectiveness of this fixation method.

Finally after 3 washes in physiologic water, the final suspension is kept and stored at a 10% concentration.

The lysoganglioside $G_{M1}$ used as a base product is prepared by hydrolysis as described by HOLMGREN, MANSSON and SVENNERHOLM, Medical Biology (1974) (52, 229, 233).

4.5 Fixation of the cholera toxin. To affix the toxin, one may proceed in an manner analogous to that described in Example 1.

EXAMPLE 5

Coupling of ganglioside $G_{M1}$ or of lysoganglioside $G_{M1}$ on latex particles followed by the cholera toxin fixation.

5.1 To three volumes of a 10% latex suspension are added to a ganglioside solution containing from 1 to 3 mg of $G_{M1}$ per ml.

The latex used is that marketed by "RHONE POULENC" under the trade name ESTAPOR.

The suspension pH is adjusted at 13 by adding a sufficient amount of normal sodium hydroxide solution.

The incubation temperature is 45° but may vary from 5° to 60° C.

The contact period is about 15 hours.

The suspension is then ultra centrifuged at 30,000 rpm for an hour.

The sialic acid dosage and the ganglioside dosage in the supernatant liquor shows that all of the $G_{M1}$ has been affixed to the latex particles.

After three washes in physiologic water to which 0.1% F Tween 80 has been added it is possible to check that all the $G_{M1}$ biologic activity has disappeared from the supernatant liquor and has not appeared in the supernatant liquor from the washes and is totally found in the residue at a final concentration of 1%.

5.2 Lysoganglioside $G_{M1}$ coupling, the same technique as for ganglioside $G_{M1}$ applies except the pH is not necessarily alkaline. A neutral pH may be just as good.

5.3 Fixation of the cholera toxin. The same procedure as in example is followed 1. However, to separate the particulate material finally obtained, the centrifugation must be replaced by ultracentrifugation in this case.

EXAMPLE 6

Coupling of the ganglioside $G_{M1}$ on active carbon particles followed by fixation of the cholera toxin.

6.1 One volume of a 30% suspension of particulate carbon is mixed with one volume of a solution of ganglioside $G_{M1}$ at a concentration ranging from 1 to 3 mg/ml. After this centrifugation, washing and recovery in a physiologic buffer at a concentration of 1%, the suspension is ready to be used for the cholera toxin fixation.

In the same manner, lysoganglioside $G_{M1}$ may be affixed in the place of ganglioside $G_{M1}$.

6.2 Fixation of the cholera toxin. The same procedures as in Example 1 are followed. If necessary, centrifugation is replaced by ultracentrifugation at 30,000 rpm for about 1 hour (in cases when the particles are colloidal). The centrifugation residue is then washed with physiologic water and this concentrated suspension may then be used (diluted) in the preparation of anticholera vaccines doses.

EXAMPLE 7

Rabbit immunization

The 10% particle suspension obtained in Example 4 is injected subcutaneously in rabbits, at a rate of 1 ml per week, for 4 weeks. Each rabbit, without exception, is immunized and synthesized anti-red corpuscles antibodies are easily eliminated by mixing the anti-serum with an equal volume of a a 50% suspension of fresh red blood corpuscles.

After this treatment one may note: (a) that the serums of rabbits so immunized only have one precipitation line with a culture filtrate rich in toxin, in double immunodiffusion; (b) that this precipitation line forms a complete identity reaction with the line obtained between a standard preparation of purified cholera toxin and the same rabbit antiserums; and (c) that this precipitation line does not exist between the rabbit serums and the same culture filtrate without toxic activity.

EXAMPLE 8

Ganglioside $G_{M1}$ or lysoganglioside $G_{M1}$ grafting onto cholera vibrios.

A suspension of cholera vibrios of the INABA type or of the OGAWA type or a mixture thereof is adjusted at a $10^9$ germs/ml concentration. This suspension is treated with either formol or glutaraldehyde, in the very same identical conditions as those described for the red blood corpuscles suspension.

The coupling technique for ganglioside and lysoganglioside $G_{M1}$ is the same as the one described for the red blood corpuscle suspension. Also, the coupling technique for the second coating (toxin) is the same as described for red blood corpuscles.

The obtained product may be lyophilised if desired.

It constitutes a vaccine which may be administered subcutaneously.

EXAMPLE 9

Fixation of the cholera toxin on carbon particles coated with ganglioside $G_{M1}$, without ganglioside saturation by the toxin.

Proceed as described in example 6 using a smaller amount of cholera toxin, 50% for example, of that which is necessary to saturate the reactive ganglioside $G_{M1}$ sites.

A suspension is obtained which, administered orally, protects persons exposed to cholera infection against said disease.

We claim:

1. A process for the preparation of a particulate material capable of inducing immunity and inducing the synthesis of antibodies to cholera toxin when administered to a living organism that possesses an immunity defense system which comprises support particles provided with a first coating of a ganglioside having an affinity for cholera toxin and a second coating of cholera toxin attached to said ganglioside coating, said support particles being selected from red blood corpuscles, inactivated bacteria particles, an organic polymer capable of giving a stable suspension in water, carbon particles or porous mineral particles coated with a polysaccharide polymer or with an oxidative scission product thereof, crosslinked or not, said process comprising in a first stage affixing said ganglioside onto said support particles to provide said first coating on said support particles and in a second stage affixing said cholera toxin onto said ganglioside coating.

2. The process of claim 1 wherein the second stage is effected by contacting the ganglioside coated particles with cholera toxin for a time ranging from 1 to 60 minutes at a temperature ranging from 0° to 60° C.

3. The process of claim 1 wherein the support particles are red blood corpuscles treated with formaldehyde or glutaraldehyde.

4. The process of claim 3 wherein the treatment of said red blood corpuscles comprises reacting said red blood corpuscles in suspension in a physiological salt solution with a physiological salt solution of formaldehyde or glutaraldehyde for a period of 15 minutes to 15 hours at a temperature ranging from 0° to 60° C., the formaldehyde or glutaraldehyde being present in an amount ranging from 0.01 to 20 grams per 100 ml of red blood corpuscle suspension.

5. The process of claim 4 wherein the thus treated red blood corpuscles are contacted with a suspension of ganglioside $G_{M1}$ at a pH equal to or greater than 8 and at an incubation temperature ranging from 0° to 60° C. for an incubation time ranging from about 1 hour to 15 hours.

6. The process of claim 5 wherein the pH is about 13, the temperature is about 45° C. and the time is about 15 hours.

7. The process of claim 4 wherein the thus treated red blood corpuscles are contacted with a suspension of lysoganglioside $G_{M1}$ at a pH above 5 and at an incubation temperature ranging from 0° to 60° C. for an incubation time ranging from 30 minutes to 30 hours.

8. The process of claim 7 wherein the pH is about 7.

9. The process of claim 1 wherein the support particle is an inactivated bacteria particle.

10. The process of claim 9 wherein the bacteria particle is cholera vibrios.

11. The process of claim 1 wherein the support particle is an organic polymer capable of giving a stable suspension in water.

12. The process of claim 11 wherein said organic polymer is styrene, butadiene or divinylbenzene.

13. The process of claim 1 wherein the support particle is a carbon particle.

14. The process of claim 1 wherein the support particle is a porous mineral particle coated with an aminopolysaccharide or an oxidative scission product thereof, crosslinked or not.

15. A process for the preparation of a particulate material capable of inducing immunity and inducing the synthesis of antibodies to cholera toxin when administered to a living organism that possesses an immunity defense system which comprises support particles provided with a first coating of a ganglioside having an affinity for cholera toxin and a second coating of cholera toxin attached to said ganglioside coating, said support particles being selected from red blood corpuscles, inactivated bacteria particles, an organic polymer capable of giving a stable suspension in water, carbon particles or porous mineral particles coated with a polysaccharide polymer or with an oxidative scission product thereof, crosslinked or not comprising in a first stage affixing said ganglioside onto said support particles to provide said first coating on said support particles and in a second stage attaching said cholera toxin onto said ganglioside coating, the amount of attached cholera toxin being such that the attachment sites of said ganglioside are not saturated with said cholera toxin.

16. An parenterally administrable medicine for inducing an immunity response to cholera toxin comprising a dosage of a particulate material capable of inducing immunity and inducing the synthesis of antibodies to cholera toxin consisting essentially of support particles selected from inactivated bacteria particles and soluble polysaccharides provided with a first coating of a ganglioside having an affinity for cholera toxin and a second coating of cholera toxin attached to said ganglioside coating, said dosage being effective to induce said immunity response.

17. A medicine for inducing an immunity response to cholera toxin comprising a dosage of a particulate material capable of inducing immunity and inducing the synthesis of antibodies to cholera when administered to a living organism that possesses an immunity defense system which consists essentially of support particles provided with a first coating of a ganglioside having an affinity for cholera toxin and a second coating of cholera toxin attached to said ganglioside coating, said dosage being effective to induce said immunity response.

18. The medicine of claim 17 wherein said support particles are selected from red blood corpuscles, polysaccharide particles, inactivated bacteria particles, an organic polymer capable of giving a stable suspension in water, carbon particles or porous mineral particles coated with a polysaccharide polymer or with an oxidative scission product thereof, crosslinked or not.

19. The medicine of claim 17 for oral administration wherein the amount of cholera toxin attached to said first coating is such that the attachment sites of said ganglioside are not saturated with said cholera toxin.

20. The medicine of claim 17 wherein the support particles are red blood corpuscles.

21. The medicine of claim 17 wherein the support particles are inactivated bacteria particles.

22. The medicine of claim 21 wherein the inactivated bacteria particles are cholera vibrios.

23. The medicine of claim 17 wherein the support particles are an organic polymer selected from styrene, butadiene and divinylbenzene.

24. The medicine of claim 17 wherein the support particles are carbon particles.

25. The medicine of claim 17 wherein the support particles are polysaccharide particles.

26. The medicine of claim 25 wherein the polysaccharide is an aminopolysaccharide.

27. The medicine of claim 17 wherein the support particles are porous mineral particles coated with an aminopolysaccharide polymer or an oxidative scission product thereof, crosslinked or not.

28. A process for inducing the formation of cholera antitoxin antibodies comprising injecting into an animal a particulate material comprising support particles provided with a first coating of a ganglioside having an affinity for cholera toxin and a second coating of cholera toxin attached to said ganglioside coating, said support particles being selected from red blood corpuscles, inactivated bacteria particles, an organic polymer capable of giving a stable suspension in water, carbon particles or porous mineral particles coated with a polysaccharide polymer or with an oxidative scission product thereof, crosslinked or not so as to induce the synthesis of said cholera antitoxin antibodies and subsequently isolating the said resulting antibodies.

29. A process for inducing an immunity response to cholera toxin comprising orally administering to a living organism possessing an immunity defense system the medicine of claim 17 in a dosage amount effective to induce said immunity response.

30. A process for inducing an immunity response to cholera toxin comprising parenterally administering to a vibrio carrying human the medicine of claim 16 in a dosage amount effective to induce said immunity response.

31. A process for inducing an immunity response to cholera toxin comprising parenterally administering to a living organism possessing an immunity defense system the medicine of claim 17 in a dosage amount effective to induce said immunity response, wherein the support particle is an inactivated bacteria particle or a polysaccharide.

* * * * *